(12) United States Patent
Saadat et al.

(10) Patent No.: US 8,512,229 B2
(45) Date of Patent: Aug. 20, 2013

(54) METHOD AND APPARATUS FOR OBTAINING ENDOLUMINAL ACCESS

(75) Inventors: Vahid Saadat, Saratoga, CA (US); Desmond Birkett, Boston, MA (US); Chris Rothe, San Jose, CA (US); Tracy Maahs, Rancho Santa Margarita, CA (US)

(73) Assignee: USGI Medical Inc., San Clemente, CA (US)

( * ) Notice: Subject to any disclaimer, the term of this patent is extended or adjusted under 35 U.S.C. 154(b) by 432 days.

(21) Appl. No.: 10/824,936

(22) Filed: Apr. 14, 2004

(65) Prior Publication Data

US 2005/0234296 A1 Oct. 20, 2005

(51) Int. Cl.
*A61B 1/00* (2006.01)

(52) U.S. Cl.
USPC ........... 600/129; 600/106; 600/111; 600/127; 600/166; 600/173

(58) Field of Classification Search
USPC ......................................... 600/101, 104, 114
See application file for complete search history.

(56) References Cited

U.S. PATENT DOCUMENTS

| | | | | |
|---|---|---|---|---|
| 5,305,121 | A | * | 4/1994 | Moll ................................ 348/45 |
| 5,954,731 | A | | 9/1999 | Yoon |
| 5,984,932 | A | | 11/1999 | Yoon |
| 5,993,466 | A | | 11/1999 | Yoon |
| 6,017,358 | A | | 1/2000 | Yoon et al. |
| 6,066,090 | A | * | 5/2000 | Yoon ............................. 600/113 |
| 6,086,601 | A | | 7/2000 | Yoon |
| 6,277,064 | B1 | | 8/2001 | Yoon |
| 6,352,503 | B1 | | 3/2002 | Matsui et al. |
| 6,761,685 | B2 | * | 7/2004 | Adams et al. .................. 600/121 |
| 6,783,491 | B2 | | 8/2004 | Saadat et al. |
| 6,790,173 | B2 | | 9/2004 | Saadat et al. |
| 6,811,532 | B2 | | 11/2004 | Ogura et al. |
| 6,821,285 | B2 | | 11/2004 | Laufer et al. |
| 6,835,199 | B2 | | 12/2004 | McGuckin, Jr. et al. |
| 6,837,847 | B2 | | 1/2005 | Ewers et al. |
| 6,837,849 | B2 | | 1/2005 | Ogura et al. |
| 6,899,673 | B2 | | 5/2005 | Ogura et al. |
| 6,942,613 | B2 | | 9/2005 | Ewers et al. |
| 6,960,162 | B2 | | 11/2005 | Saadat et al. |
| 6,960,163 | B2 | | 11/2005 | Ewers et al. |
| 6,991,602 | B2 | | 1/2006 | Nakazawa et al. |

(Continued)

FOREIGN PATENT DOCUMENTS

| | | |
|---|---|---|
| EP | 1585428 | 9/2005 |
| EP | 1583462 | 10/2005 |

(Continued)

OTHER PUBLICATIONS

Mason, "Development of Future of Gastroplasties for Morbid Obesity," *Arch Surg*, vol. 138 (Apr. 2003), pp. 362-366.

*Primary Examiner* — Matthew J Kasztejna
(74) *Attorney, Agent, or Firm* — Kenneth H. Ohriner; Perkins Coie LLP

(57) ABSTRACT

The present invention provides methods and apparatus for obtaining endoluminal access. An elongate body is configured for insertion within a body lumen, conduit, organ, orifice or passageway, the elongate body having a working axis and a distal region, and an articulating element disposed near the distal region, the articulating element configured to articulate off-axis from the working axis of the elongate body. Methods of using apparatus of the present invention are also provided.

27 Claims, 6 Drawing Sheets

(56) References Cited

U.S. PATENT DOCUMENTS

| | | |
|---|---|---|
| 7,041,052 B2 | 5/2006 | Saadat et al. |
| 7,128,708 B2 | 10/2006 | Saadat et al. |
| 7,160,312 B2 | 1/2007 | Saadat |
| 2002/0120253 A1 | 8/2002 | Ouchi |
| 2003/0109892 A1 | 6/2003 | Deem et al. |
| 2004/0059346 A1 | 3/2004 | Adams et al. |
| 2004/0116897 A1 | 6/2004 | Aboul-Hosn |
| 2004/0116949 A1 | 6/2004 | Ewers et al. |
| 2004/0122290 A1* | 6/2004 | Irion et al. .................... 600/171 |
| 2004/0122456 A1 | 6/2004 | Saadat et al. |
| 2004/0122473 A1 | 6/2004 | Ewers et al. |
| 2004/0138525 A1* | 7/2004 | Saadat et al. .................. 600/104 |
| 2004/0138529 A1 | 7/2004 | Wiltshire et al. |
| 2004/0147958 A1 | 7/2004 | Lam et al. |
| 2004/0162568 A1 | 8/2004 | Saadat et al. |
| 2004/0167546 A1 | 8/2004 | Saadat et al. |
| 2004/0186349 A1 | 9/2004 | Ewers et al. |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0210243 A1 | 10/2004 | Gannoe et al. |
| 2004/0215216 A1 | 10/2004 | Gannoe et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0249362 A1 | 12/2004 | Levine et al. |
| 2004/0249367 A1 | 12/2004 | Saadat et al. |
| 2005/0020901 A1 | 1/2005 | Belson et al. |
| 2005/0033320 A1 | 2/2005 | McGuckin, Jr. et al. |
| 2005/0033328 A1 | 2/2005 | Laufer et al. |
| 2005/0043758 A1 | 2/2005 | Golden et al. |
| 2005/0049617 A1 | 3/2005 | Chatlynne et al. |
| 2005/0065397 A1 | 3/2005 | Saadat et al. |
| 2005/0065401 A1 | 3/2005 | Saadat et al. |
| 2005/0065536 A1 | 3/2005 | Ewers et al. |
| 2005/0075653 A1 | 4/2005 | Saadat et al. |
| 2005/0096502 A1* | 5/2005 | Khalili ........................ 600/106 |
| 2005/0107663 A1 | 5/2005 | Saadat et al. |
| 2005/0113640 A1 | 5/2005 | Saadat et al. |
| 2005/0119524 A1 | 6/2005 | Sekine et al. |
| 2005/0119671 A1 | 6/2005 | Reydel et al. |
| 2005/0137455 A1 | 6/2005 | Ewers et al. |
| 2005/0165272 A1 | 7/2005 | Okada et al. |
| 2005/0192629 A1 | 9/2005 | Saadat et al. |
| 2005/0203488 A1 | 9/2005 | Michlitsch et al. |
| 2005/0203489 A1 | 9/2005 | Saadat et al. |
| 2005/0203500 A1 | 9/2005 | Saadat et al. |
| 2005/0222495 A1 | 10/2005 | Okada et al. |
| 2005/0228224 A1 | 10/2005 | Okada et al. |
| 2005/0234294 A1 | 10/2005 | Saadat et al. |
| 2005/0234296 A1 | 10/2005 | Saadat et al. |
| 2005/0245945 A1 | 11/2005 | Ewers et al. |
| 2005/0250980 A1 | 11/2005 | Swanstrom et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |
| 2005/0250988 A1 | 11/2005 | Ewers et al. |
| 2005/0250990 A1 | 11/2005 | Le et al. |
| 2005/0251091 A1 | 11/2005 | Saadat et al. |
| 2005/0251157 A1 | 11/2005 | Saadat et al. |
| 2005/0251158 A1 | 11/2005 | Saadat et al. |
| 2005/0251159 A1 | 11/2005 | Ewers et al. |
| 2005/0251160 A1 | 11/2005 | Saadat et al. |
| 2005/0251161 A1 | 11/2005 | Saadat et al. |
| 2005/0251162 A1 | 11/2005 | Rothe et al. |
| 2005/0251165 A1 | 11/2005 | Vaughan et al. |
| 2005/0251166 A1 | 11/2005 | Vaughan et al. |
| 2005/0251176 A1 | 11/2005 | Swanstrom et al. |
| 2005/0251177 A1 | 11/2005 | Saadat et al. |
| 2005/0251189 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267335 A1 | 12/2005 | Okada et al. |
| 2005/0272977 A1 | 12/2005 | Saadat et al. |
| 2005/0277945 A1 | 12/2005 | Saadat et al. |
| 2005/0277966 A1 | 12/2005 | Ewers et al. |
| 2005/0277975 A1 | 12/2005 | Saadat et al. |
| 2005/0277981 A1 | 12/2005 | Maahs et al. |
| 2005/0277983 A1 | 12/2005 | Saadat et al. |
| 2006/0009789 A1 | 1/2006 | Gambale et al. |
| 2006/0020274 A1 | 1/2006 | Ewers et al. |
| 2006/0020276 A1 | 1/2006 | Saadat et al. |
| 2006/0058582 A1 | 3/2006 | Maahs et al. |
| 2006/0100480 A1 | 5/2006 | Ewers et al. |
| 2006/0100579 A1 | 5/2006 | Maahs et al. |
| 2006/0111614 A1 | 5/2006 | Saadat et al. |
| 2006/0135971 A1 | 6/2006 | Swanstrom et al. |
| 2006/0157067 A1 | 7/2006 | Saadat et al. |
| 2006/0161185 A1 | 7/2006 | Saadat et al. |
| 2006/0178560 A1 | 8/2006 | Saadat et al. |
| 2006/0178562 A1 | 8/2006 | Saadat et al. |
| 2006/0183975 A1 | 8/2006 | Saadat et al. |
| 2006/0184161 A1 | 8/2006 | Maahs et al. |
| 2006/0189845 A1 | 8/2006 | Maahs et al. |
| 2006/0217762 A1 | 9/2006 | Maahs et al. |
| 2006/0237022 A1 | 10/2006 | Chen et al. |
| 2006/0237023 A1 | 10/2006 | Cox et al. |
| 2006/0258909 A1 | 11/2006 | Saadat et al. |
| 2006/0271073 A1 | 11/2006 | Lam et al. |
| 2006/0271074 A1 | 11/2006 | Ewers et al. |
| 2006/0271101 A1 | 11/2006 | Saadat et al. |
| 2006/0287666 A1 | 12/2006 | Saadat et al. |
| 2007/0015965 A1 | 1/2007 | Cox et al. |
| 2007/0079924 A1 | 4/2007 | Saadat et al. |
| 2007/0123840 A1 | 5/2007 | Cox |
| 2007/0142849 A1 | 6/2007 | Ewers et al. |

FOREIGN PATENT DOCUMENTS

| | | |
|---|---|---|
| EP | 1648279 | 4/2006 |
| EP | 1699366 | 9/2006 |
| EP | 1781184 | 5/2007 |
| EP | 1804680 | 7/2007 |
| EP | 1804683 | 7/2007 |
| EP | 1863389 | 12/2007 |
| EP | 1868484 | 12/2007 |
| JP | 06-054796 A | 3/1994 |
| JP | 2006-512935 | 4/2006 |
| JP | 2007-513717 | 5/2007 |
| JP | 2007-521033 | 8/2007 |
| JP | 2007-532240 | 11/2007 |
| WO | WO 02/060328 A1 | 8/2002 |
| WO | WO 03/092509 A1 | 11/2003 |
| WO | WO 03/094785 A1 | 11/2003 |
| WO | WO 2004/019788 A2 | 3/2004 |
| WO | WO 2004/021894 A1 | 3/2004 |
| WO | WO 2004/041119 | 5/2004 |
| WO | WO 2004/004542 A2 | 6/2004 |
| WO | WO 2004/050971 A2 | 6/2004 |
| WO | WO 2004/064600 | 8/2004 |
| WO | WO 2004/084808 A2 | 10/2004 |
| WO | WO 2004/103430 | 12/2004 |
| WO | WO 2004/110285 A1 | 12/2004 |
| WO | WO 2005/011463 | 2/2005 |
| WO | WO 2005/011519 | 2/2005 |
| WO | WO 2005/037152 A1 | 4/2005 |
| WO | WO 2005/048815 A2 | 6/2005 |
| WO | WO 2005/053517 A1 | 6/2005 |
| WO | WO 2005/058239 | 6/2005 |
| WO | WO 2005/086945 | 9/2005 |
| WO | WO 2005/104927 | 11/2005 |
| WO | WO 2005/110244 | 11/2005 |
| WO | WO 2005/122914 | 12/2005 |
| WO | WO 2005/122915 | 12/2005 |

| | | | | | |
|---|---|---|---|---|---|
| WO | WO 2006/019868 | 2/2006 | WO | WO 2006/093975 | 9/2006 |
| WO | WO 2006/039199 | 4/2006 | WO | WO 2006/110275 | 10/2006 |
| WO | WO 2006/039223 | 4/2006 | WO | WO 2006/127306 | 11/2006 |
| WO | WO 2006/039296 | 4/2006 | WO | WO 2007/009021 | 1/2007 |
| WO | WO 2006/078429 | 7/2006 | | | |
| WO | WO 2006/089217 | 8/2006 | | | |

* cited by examiner

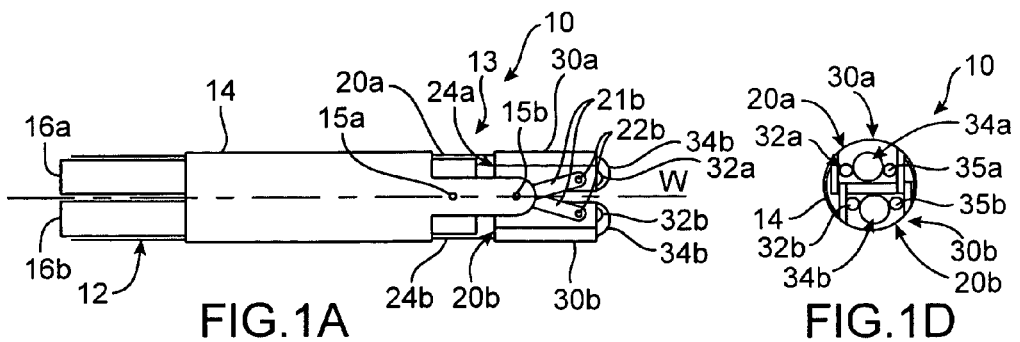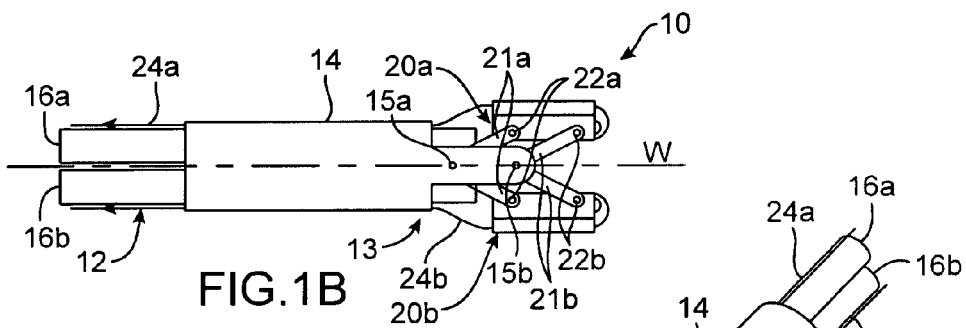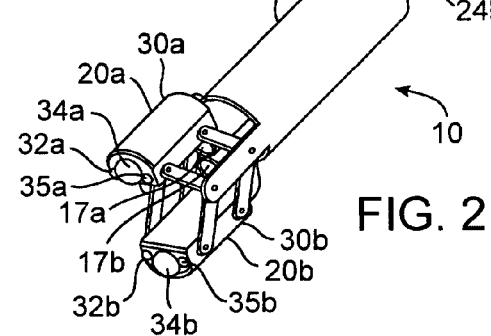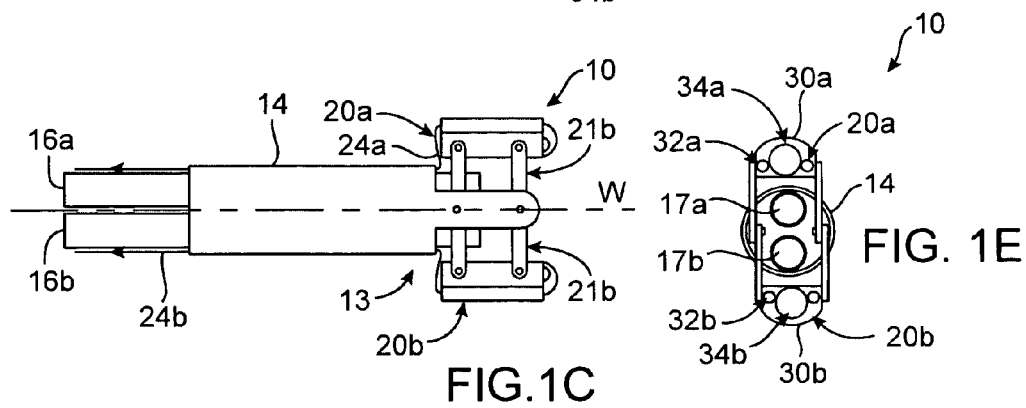

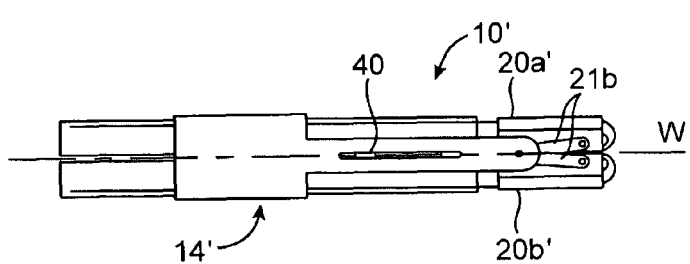
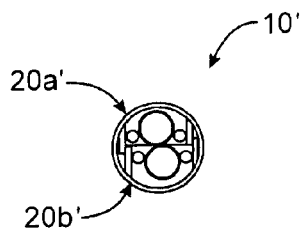
FIG. 3A  FIG. 3D
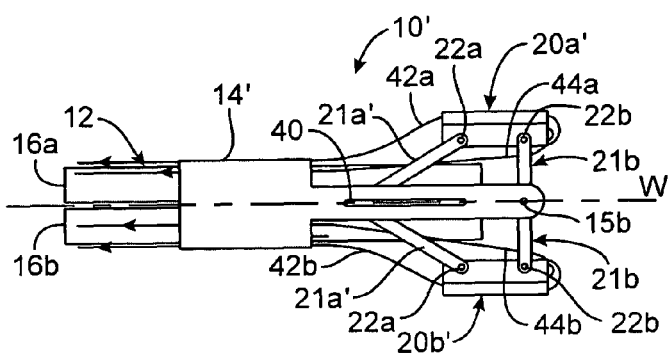
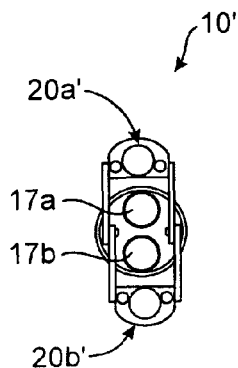
FIG. 3B  FIG. 3E
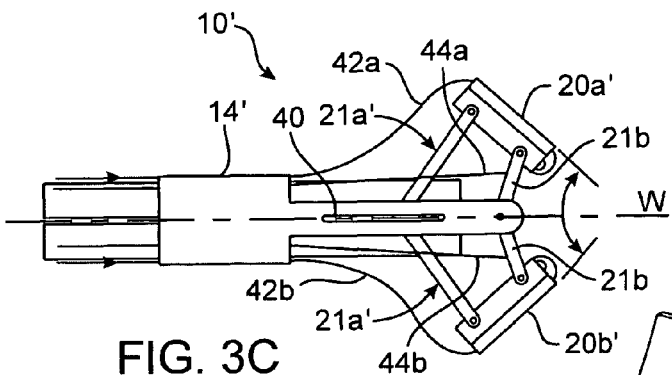
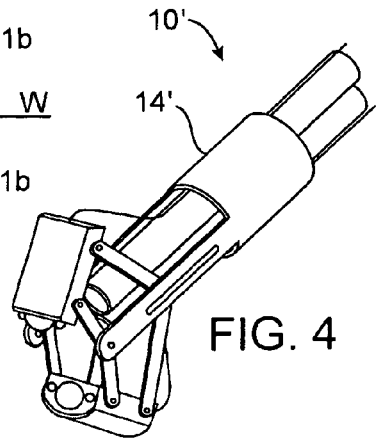
FIG. 3C  FIG. 4

METHOD AND APPARATUS FOR OBTAINING ENDOLUMINAL ACCESS

BACKGROUND OF THE INVENTION

Field of the Invention

The present invention relates to methods and apparatus for obtaining endoluminal access. More particularly, the present invention relates to methods and apparatus for obtaining endoluminal access utilizing off-axis articulation.

Medical endoscopy entails the insertion of an elongate body into a body lumen, conduit, organ, orifice, passageway, etc. The elongate body typically has a longitudinal or working axis and a distal region, and a visualization element disposed near the distal region in-line with the working axis. The visualization element may comprise an optical fiber that extends through the elongate body, or a video chip having an imaging sensor, the video chip coupled to or including a signal-processing unit that converts signals obtained by the imaging sensor into an image. The elongate body may also include a working lumen to facilitate passage of diagnostic or therapeutic tools therethrough, or for injection of fluids or to draw suction.

The maximum delivery profile for a medical endoscope may be limited by the cross-sectional profile of the body lumen, conduit, organ, orifice, passageway, etc., in which the endoscope is disposed. At the same time, advances in therapeutic endoscopy have led to an increase in the complexity of operations attempted with endoscopes, as well as the complexity of tools advanced through the working lumens of endoscopes. As tool complexity has increased, a need has arisen in the art for endoscopes having relatively small delivery profiles that allow access through small body lumens, but that have relatively large working lumens that enable passage of complex diagnostic or therapeutic tools. Furthermore, as the complexity of operations attempted with endoscopes has increased, there has arisen a need for enhanced visualization platforms, including three-dimensional or stereoscopic visualization platforms.

In view of the foregoing, it would be desirable to provide methods and apparatus for obtaining endoluminal access that facilitate introduction of the apparatus into relatively small body lumens, while providing for introduction of at least one relatively large tool, as compared to a standard endoscope.

Medical endoscopy entails the insertion of an elongate body into a body lumen, conduit, organ, orifice, passageway, etc. The elongate body typically has a longitudinal or working axis and a distal region, and a visualization element disposed near the distal region in-line with the working axis. The visualization element may comprise an optical fiber that extends through the elongate body, or a video chip having an imaging sensor, the video chip coupled to or including a signal-processing unit that converts signals obtained by the imaging sensor into an image. The elongate body may also include a working lumen to facilitate passage of diagnostic or therapeutic tools therethrough, or for injection of fluids or to draw suction.

The maximum delivery profile for a medical endoscope may be limited by the cross-sectional profile of the body lumen, conduit, organ, orifice, passageway, etc., in which the endoscope is disposed. At the same time, advances in therapeutic endoscopy have led to an increase in the complexity of operations attempted with endoscopes, as well as the complexity of tools advanced through the working lumens of endoscopes. As tool complexity has increased, a need has arisen in the art for endoscopes having relatively small delivery profiles that allow access through small body lumens, but that have relatively large working lumens that enable passage of complex diagnostic or therapeutic tools. Furthermore, as the complexity of operations attempted with endoscopes has increased, there has arisen a need for enhanced visualization platforms, including three-dimensional or stereoscopic visualization platforms.

In view of the foregoing, it would be desirable to provide methods and apparatus for obtaining endoluminal access that facilitate introduction of the apparatus into relatively small body lumens, while providing for introduction of at least one relatively large tool, as compared to a standard endoscope.

It would be desirable to provide methods and apparatus for obtaining endoluminal access that facilitate stereoscopic visualization.

BRIEF SUMMARY OF THE INVENTION

Endoluminal access that facilitates introduction of the apparatus into relatively small body lumens while providing for introduction of at least one relatively large tool, as compared to a standard endoscope, may be accomplished by providing an elongate body configured for insertion within a body lumen, conduit, organ, orifice, passageway, etc. The elongate body has a working or main longitudinal axis and a distal region, and at least one articulating element disposed near or at the distal region. The articulating element is generally configured to articulate off-axis or out-of-line from the working axis of the elongate body such that the element (or elements) are extendable and retractable in a radial direction relative to the working axis. The element may comprise, for example, the distal region of a working lumen extending through the elongate body; a visualization element, such as a fiber optic or video chip; a diagnostic or therapeutic tool; or an illumination element. Additional alternative articulating elements will be apparent to one of skill in the art. Alternatively, the articulating elements may simply act as radially extendable platforms from which various tools may be advanced or therapies may be conducted. This extendable platform may allow for the user to deploy the elements once the apparatus has been desirably situated within the body giving the user a versatile platform from which to access a greater portion of the body lumen while maintaining a device having a relatively small delivery profile.

Advantageously, the articulating element provides the elongate body with a collapsed delivery configuration and a radially expanded deployed configuration. The collapsed delivery profile may facilitate passage of the elongate body within small body lumens, cavities, etc., while the expanded deployed profile may facilitate diagnosis or therapy via the elongate body once the elongate body is disposed within the body lumen. For example, off-axis articulation of the articulating element may expose distal openings of one or more working lumens extending through the elongate body.

With traditional endoscopes, a maximum profile of the working lumen is constrained by geometry of the visualization element. Conversely, the apparatus described herein enables one or more visualization elements, working lumens, tools, illumination elements, etc., to be aligned with the working axis of the elongate body in the delivery configuration, and articulated out of alignment in the radially deployed configuration, thereby significantly reducing geometric constraints. As will be apparent, the working lumen(s), tool(s), illumination elements and visualization element(s) optionally may be provided as part of multiple distinct devices. For example, a standard endoscope may be provided as a visualization element, while one or more working lumens may be disposed within an overtube or endoluminal tool deployment system (e.g., as described in Applicant's co-pending U.S. patent application Ser. No. 10/797,485, filed Mar. 9, 2004, which is incorporated herein by reference in its entirety) disposed over the standard endoscope.

Optionally, multiple articulating elements may be provided near the distal region of the elongate body. When the multiple articulating elements comprise two or more visualization elements, stereoscopic visualization may be provided. When the multiple elements comprise multiple working lumens or tools, complex therapeutic or diagnostic endoluminal procedures may be performed. Combinations of various articulating elements may be provided.

BRIEF DESCRIPTION OF THE DRAWINGS

FIGS. 1A-1E are side and frontal views of one variation of the apparatus, illustratively showing the articulating elements in collapsed delivery configurations, partially articulated configurations and expanded deployed configurations;

FIG. 2 is a perspective view of the apparatus of FIG. 1C;

FIGS. 3A-3E are side and frontal views of an alternative variation of the apparatus of FIGS. 1A-1E, shown, respectively, in collapsed, partially articulated, and expanded configurations;

FIG. 4 is a perspective view of the apparatus of FIG. 3C;

DETAILED DESCRIPTION OF THE INVENTION

Figure 5:
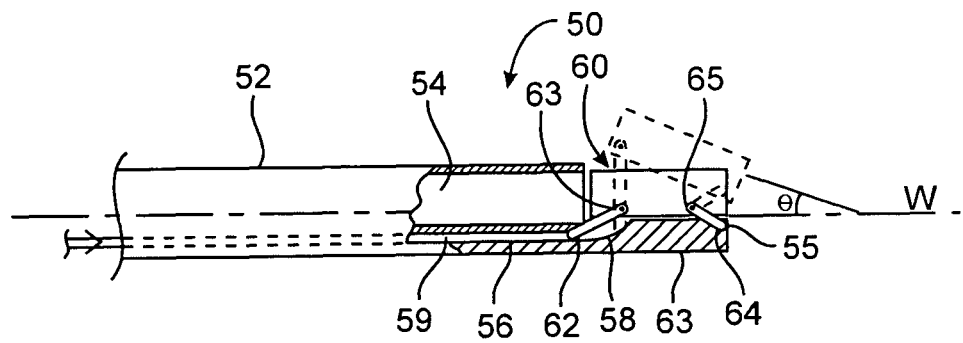
FIG. 5 is a schematic, side view, partially in cut-away section, of an alternative variation comprising articulation biasing.

Endoluminal access may be achieved more effectively by utilizing off-axis articulation with an apparatus advanced within a body lumen. As described herein, off-axis articulating elements may act as radially extendable platforms from which various tools may be advanced or therapies may be conducted. This extendable platform may allow for the user to deploy the elements once the apparatus has been desirably situated within the body giving the user a versatile platform from which to access a greater portion of the body lumen while maintaining a device having a relatively small delivery profile.

With reference to FIGS. 1A-1E and 2, a first variation of the apparatus is shown. Apparatus 10 comprises elongate body 12 configured for insertion within a body lumen, conduit, organ, orifice or passageway. Elongate body 12 may, for example, comprise a steerable, rigidizable and/or multi-segmented body, such as described in co-pending U.S. patent application Ser. No. 10/797,485 filed Mar. 9, 2004, which has been incorporated by reference above. Body 12 comprises working axis W and distal region 13. Apparatus 10 further comprises at least one articulating element 20, shown in this example as two elements 20a and 20b (collectively referred to as elements 20), disposed near or at distal region 13 of body 12.

Elongate body 12 further comprises housing 14, which may be slidably disposed over one or more working lumens 16, illustratively shown as working lumens 16a and 16b. Either lumen may be an insufflation lumen. Articulating elements 20 may be pivotally coupled to housing 14 by linkages 21a and 21b, which extend between hinges 22a and 22b of elements 20a and 20b and hinges 15a and 15b, respectively, of housing 14. Push/pull members 24a and 24b may also be provided to actuate articulating elements 20a and 20b, respectively, between the collapsed profile and radially extended profile.

Members 24a and 24b may extend along elongate body 12, for example, between housing 14 and lumens 16, to a proximal region of the elongate body (not shown) for manipulation by a medical practitioner. The members may be coupled to one another for coordinated actuation of articulating elements 20, or may be decoupled for independent actuation. Furthermore, the members may comprise cables or coils, as described hereinafter, adapted to convey control elements between the articulating elements and the elongate body.

As seen in FIGS. 1A-1E and 2, articulating elements 20 are configured to articulate off-axis or out-of-line from working axis W of elongate body 12. FIG. 1A shows articulating elements 20 in a collapsed delivery configuration having a reduced delivery profile suited for delivery within a body orifice, lumen, cavity, etc. FIG. 1B shows articulating elements 20 in a partially articulated configuration. FIGS. 1C and 2 show the articulating elements fully articulated to a deployed configuration of expanded profile.

Articulating elements 20 may be articulated from the reduced profile of FIG. 1A to the expanded profile of FIG. 1C by retracting members 24 relative to housing 14. The articulating elements may be articulated back to the collapsed profile, as desired, by advancing members 24 relative to housing 14. As will be apparent, elements 20 alternatively may be articulated by advancing or retracting housing 14 relative to members 24.

As seen in FIGS. 1C and 2, articulation of elements 20 to the expanded deployed configuration advantageously exposes distal openings 17a and 17b of working lumens 16a and 16b, respectively. In the delivery configuration of FIG. 1A, the lumens and articulating elements are aligned with working axis W of elongate body 12. Such alignment reduces the delivery profile of apparatus 10, but also causes articulating elements 20 to be disposed in-line with lumens 16, thereby blocking distal openings 17 of the lumens.

Articulating elements 20 off-axis and out of alignment with working axis W exposes distal openings 17 of lumens 16. Once exposed, lumens 16 may be used for passage of diagnostic or therapeutic tools from the proximal to the distal region of apparatus 10, as well as to draw suction, inject fluids, etc. By providing apparatus 10 with elements that articulate, lumens 16 may be provided with larger cross-sectional profiles than otherwise would be possible for a given delivery profile, as compared to apparatus having needed elements that cannot articulate.

Each articulating element 20 may comprise, for example, the distal region of a working lumen extending through elongate body 12. Alternatively, each articulating element may comprise a visualization element, such as a fiber optic or video chip. As yet another alternative, each articulating element may comprise a diagnostic or therapeutic tool, or an illumination element. Additional alternative articulating elements will be apparent.

In FIGS. 1A-1E and 2, articulating elements 20 illustratively comprise visualization elements 30a and 30b. Elements 30 may comprise illumination sources 32a and 32b, as well as optics 34a and 34b. Optional flushing elements 35 may also be provided. Optional illumination sources 32 may be used to provide light for imaging with elements 30, while optics 34 may, for example, comprise lenses, filters, etc. The optics may be coupled to one or more optical fibers that transmit visual information to a proximal region of apparatus 10. Control elements for visualization elements 30, such as electrical wires, flushing lumens, etc., may run within or along push/pull members 24.

Alternatively, video chips having imaging sensors may be coupled to optics 34. The chips may be adapted to receive, as well as transmit and/or signal process, visual information. Illustrative imaging sensors that may be used as part of visualization elements 30 include, but are not limited to, charge coupled device ("CCD") image sensors, complementary metal oxide semiconductor ("CMOS") image sensors, multi-layer solid state image sensors, direct image sensors, and combinations thereof. The video chips may wirelessly transmit signals to a processing and/or display unit, or one or more wires may extend along the length of the elongate body to carry such signals.

Since apparatus 10 has two articulating visualization elements 30, the apparatus 10 is adapted to provide stereoscopic or 3-dimensional visualization. Stereoscopic visualization may, for example, be displayed to a medical practitioner via a viewfinder disposed in front of the practitioner's eyes, or on a standard monitor. A depth of field, a focal point or depth, and/or a field of view of stereoscopic images produced with visualization elements 30 may be altered, for example, by changing a degree of articulation of elements 30, by varying parameters of optics 34, via digital signal processing techniques, etc.

Referring now to FIGS. 3A-3E and 4, an alternative variation of apparatus 10 is described. Apparatus 10' comprises housing 14' having at least one slot 40. Linkages 21a' extend between hinges 22a of elements 20' and slot 40 of housing 14'. In this variation, linkages 21a' are longer than more distal linkages 21b, and are slidably disposed within slot 40 of the housing. Apparatus 10' further comprises proximal push/pull members 42a and 42b coupled to the proximal regions of articulating elements 20a and 20b, respectively, as well as distal push/pull members 44a and 44b coupled to the distal regions of elements 20.

As seen in FIGS. 3A-3E, actuation of articulating elements 20a' and 20b' may be achieved by coordinated movements of proximal members 42a and 42b, distal members 44a and 44b and housing 14'. In FIG. 3A, apparatus 10' is disposed in the collapsed delivery configuration suitable for advancement within a body lumen. In FIG. 3B, members 42a and 42b and 44a and 44b have been retracted relative to housing 14', thereby causing long linkages 21a' to articulate about hinges 22a of elements 20' and to slide proximally within slot 40 of housing 14' while linkages 21b articulate about hinges 15b and 22b. Elements 20a' and 20b' articulate out of alignment and off-axis from working axis W of elongate body 12, thereby exposing distal openings 17a and 17b of lumens 16a and 16b.

As seen in FIGS. 3C and 4, subsequent advancement of proximal members 42a and 42b relative to housing 14' and distal members 44a and 44b causes long linkages 21a' to slide distally within slot 40 and articulate about hinges 22a. Such movement causes the distal regions of elements 20' to articulate inwards relative to the proximal regions of the elements, thereby changing the relative angle between elements 20a' and 20b'. As will be apparent, elements 20a' and 20b' may be articulated in either a coordinated fashion or individually.

When elements 20a' and 20b' comprise visualization elements (optionally used in a stereoscopic fashion), relative angulation of the elements may be used to dynamically alter a focal point or depth, a depth of field and/or a field of view provided by the elements. When the elements comprise tools (e.g. grasping tool arms, cutting tools, plicating tools, affixing tools) or lumens, the tools or lumens may be angled for better positioning of the tools/lumens. When the elements comprise illumination elements, angling may better light a region of interest. As will be apparent, any combination of various articulating and/or angle-able elements 20 may be provided, including combinations of visualization elements, illumination elements, tools, lumens, etc.

Referring now to FIG. 5, an alternative variation is described comprising articulation biasing. Apparatus 50 comprises elongate body 52 having working axis W, distal region 53, working lumen 54, control lumen 56 and ramp 58. Apparatus 50 may further comprise articulating element 60 disposed near or at distal region 53 of body 52. Articulating element 60 is coupled to elongate body 52 by proximal linkage 62 and torsion spring 64. Linkage 62 extends between hinge 63 of articulating element 60 and control rod 59 disposed within control lumen 56 of body 52. Torsion spring 64 extends between hinge 65 of the articulating element and hinge 55 of the elongate body. Torsion spring 64 provides element 60 with articulation biasing. In other variations, other biasing elements aside from torsion springs may be utilized.

As seen in dotted profile in FIG. 5, advancement of control rod 59 relative to elongate body 52 advances linkage 62 along ramp 58 and articulates element 60, thereby exposing the distal end of lumen 54. Torsion spring 64 has a natural tendency to push element 60 off-axis and biases the element 60 to the articulated position. Once element 60 has 'sprung-up' to the articulated position, further advancement of rod 59 controls the angle Θ of element 60 relative to elongate body 52. Retraction of rod 59 may overcome the articulation biasing of spring 64 and return apparatus 50 to the collapsed delivery configuration. The spring constant of torsion spring 64 may be specified to control a degree of articulation biasing provided by the spring.

Figure 6:
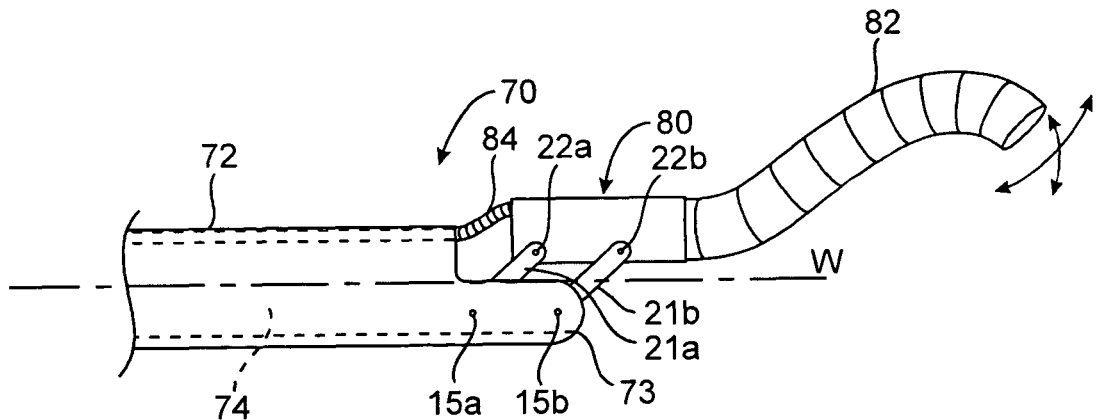
FIG. 6 is a schematic side view of an alternative variation comprising an articulating element having a steerable shaft.

Referring now to FIG. 6, another variation is described wherein the articulating element comprises a steerable shaft. Apparatus 70 comprises elongate body 72 having working axis W, distal region 73 and lumen 74. Apparatus 70 further comprises articulating element 80 disposed near distal region 73 of elongate body 72. Element 80 is coupled to the elongate body by previously-described linkages 21 disposed between hinges 15 and 22.

Articulating element 80 comprises steerable shaft 82. Shaft 82 may be a passively articulatable shaft or it may alternatively be an actively controllable shaft. Any number of conventional methods may be utilized to articulate the shape and configuration of shaft 82. In FIG. 6, shaft 82 illustratively may, for example, be steerable in any number of directions. In this variation, shaft 82 may be steerable in at least four directions, e.g., via four control wires routed through or along cable 84 and elongate body 72 to a proximal region of apparatus 70 for manipulation by a medical practitioner. Cable 84 may also be used to articulate element 80. As discussed hereinbelow with respect to FIGS. 11 and 12, proximal of cable 84, the control wires for steerable shaft 82 preferably are routed through or along body 72 in spaces that would not be usable as working lumens or for tool insertion.

During delivery, articulating element 80 and steerable shaft 82 preferably are aligned with working axis W of elongate body 72. Advantageously, the ability to articulate element 80 off-axis post-delivery allows apparatus 70 to have both a large working lumen 74 and a small collapsed delivery profile. Furthermore, steerable shaft 82 gives the apparatus an off-axis platform with added functionality for performing complex procedures. The steering capability of shaft 82 may be used to steer therapeutic or diagnostic tools, illumination, visualization, fluid flushing, suction, etc., into better position for conducting such procedures.

Various methods and apparatus for controlling elements used in conjunction with shaft 82 may be routed through cable 84 along with the control wires for shaft 82. For example, when a visualization element is coupled to steerable shaft 82, electrical wires may run through cable 84 for sending and/or receiving signals, power, etc., to/from the visualization element. In such a variation, the visualization element would allow direct visualization during insertion within a body lumen, while providing off-axis visualization and steering, as well as facilitating tool introduction, post-articulation. Alternatively or additionally, when a working lumen is disposed through steerable shaft 82, cable 84 may comprise a lumen for connecting the shaft lumen to a lumen extending through elongate body 72 of apparatus 70.

Figure 7:
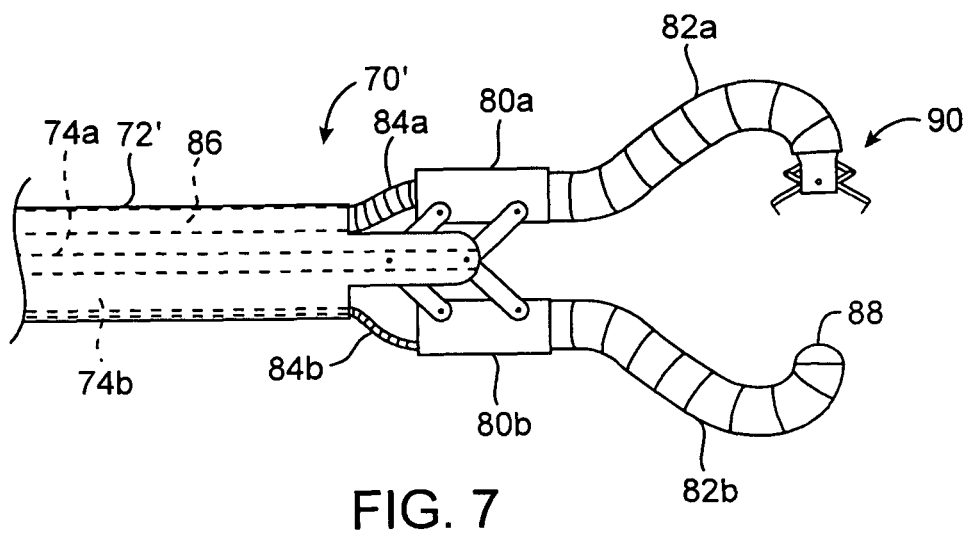
FIG. 7 is a schematic side view of an alternative variation of the apparatus of FIG. 6 comprising multiple articulating elements having steerable shafts.

Referring now to FIG. 7, an alternative variation of apparatus 70 is described comprising multiple articulating elements having steerable shafts. Apparatus 70' comprises first articulating element 80*a* and second articulating element 80*b*. Elements 80 comprise first steerable shaft 82*a* and second steerable shaft 82*b*, respectively. Lumens 74*a* and 74*b* extend through elongate body 72' and are exposed upon articulation of elements 80*a* and 80*b*, respectively. As will be apparent, a single lumen or more than two lumens alternatively may be provided. Likewise, more than two articulating elements and/or steerable shafts optionally may be provided.

In FIG. 7, first steerable shaft 82*a* illustratively is shown with working lumen 86 that extends through the shaft, as well as through cable 84*a* and elongate body 72'. Exemplary grasper tool 90 is shown advanced through lumen 86. Second steerable shaft 82*b* illustratively is shown with visualization element 88 coupled to an end thereof. Electrical wires, e.g., for powering and transmitting signals to/from the visualization element, are disposed within cable 84*b*. As will be apparent, steerable shafts 82 may be provided with additional or alternative capabilities.

Figure 8A:
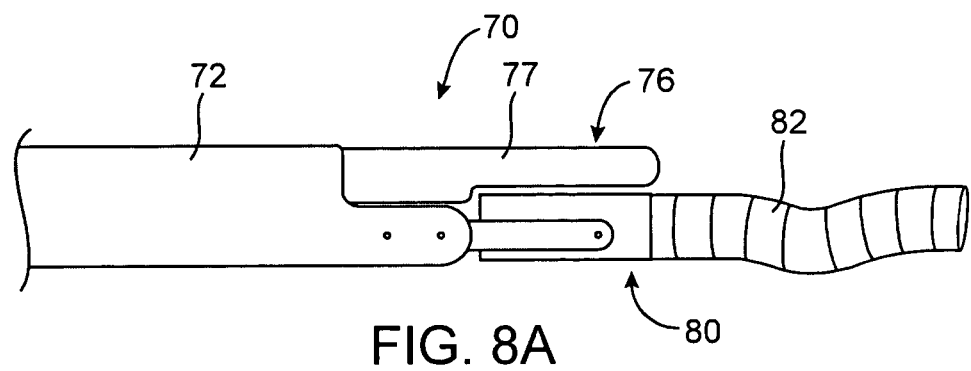
FIGS. 8A and 8B are schematic side views of illustrative variations of a traumatic tips for use with the apparatus.

With reference to FIG. 8, illustrative embodiments of atraumatic tips for use with apparatus of the present invention are described. In FIG. 8A, apparatus 70 of FIG. 6 is shown with atraumatic tip 76. Tip 76 provides a smooth transition between elongate body 72 and articulating element 80 with steerable shaft 82. Tip 76 may, for example, comprise an inflatable balloon that may be inflated as shown during insertion and delivery of apparatus 70, then deflated prior to articulation of element 80 and off-axis steering of shaft 82, so as not to block or impede articulation or the distal opening of the lumen 74 post-articulation.

Figure 8B:
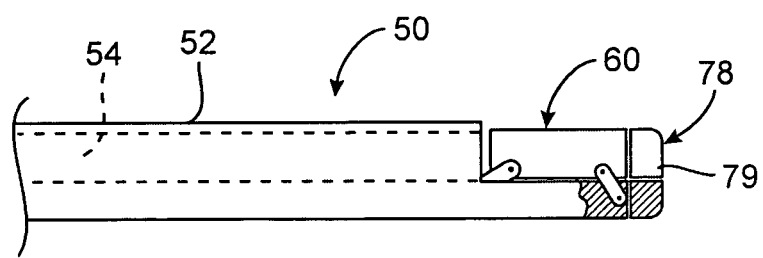

In FIG. 8B, apparatus 50 of FIG. 5 comprises alternative atraumatic tip 78 having cap 79, which optionally may be fabricated from rubber. As illustrated by the cut-away section in FIG. 8B, the cap may be U-shaped to both provide a smooth transition between elongate body 52 and articulating element 60 in the delivery configuration, as well as to ensure that the cap does not block or impede lumen 54 post-articulation.

Figure 9A:
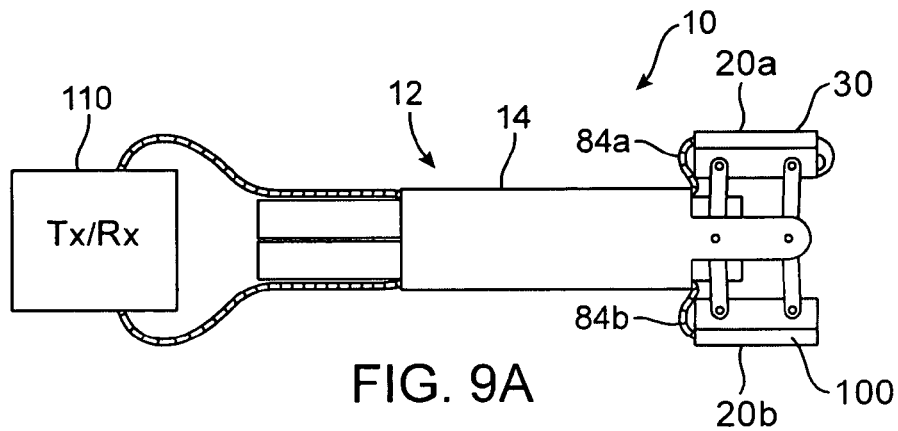
FIGS. 9A and 9B are schematic side and detail views, respectively, of a variation of the apparatus of FIGS. 1A-1E and 2 comprising an illumination articulating element and a visualization articulating element.
Figure 9B:
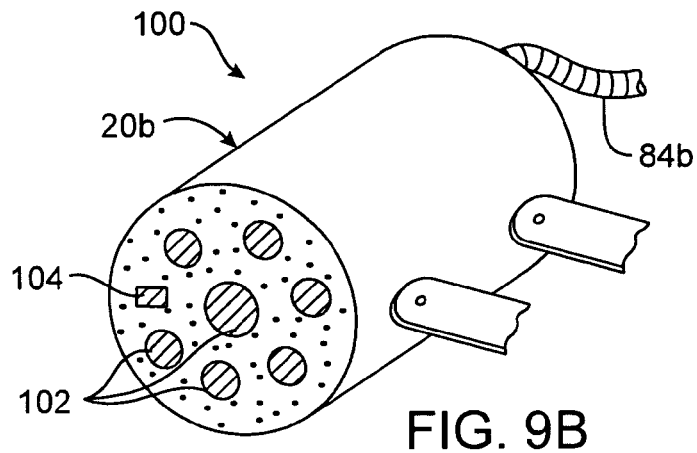

With reference now to FIG. 9, a variation of the apparatus of FIGS. 1A-1E and 2 is described comprising an articulating illumination element and an articulating visualization element. In FIG. 9A, articulating element 20*a* of apparatus 10 comprises previously described visualization articulating element 30, while articulating element 20*b* comprises illumination articulating element 100. Control wires for both element 30 and element 100, illustratively routed through coils or cables 84, are proximally coupled to control/power unit 110. As seen in FIG. 9B, illumination element 100 comprises at least one light emitting diode ("LED") 102, as well as optional sensor 104. Other variations may utilize other types of lights or illumination methods, e.g., incandescent lights, fluorescent lights or chemicals, etc. Control unit 110 may coordinate signals from visualization element 30 and sensor 104 to appropriately set the white balance of visualization element 30, as well as the intensity of light emitted from LEDs 102, etc.

Figure 10:
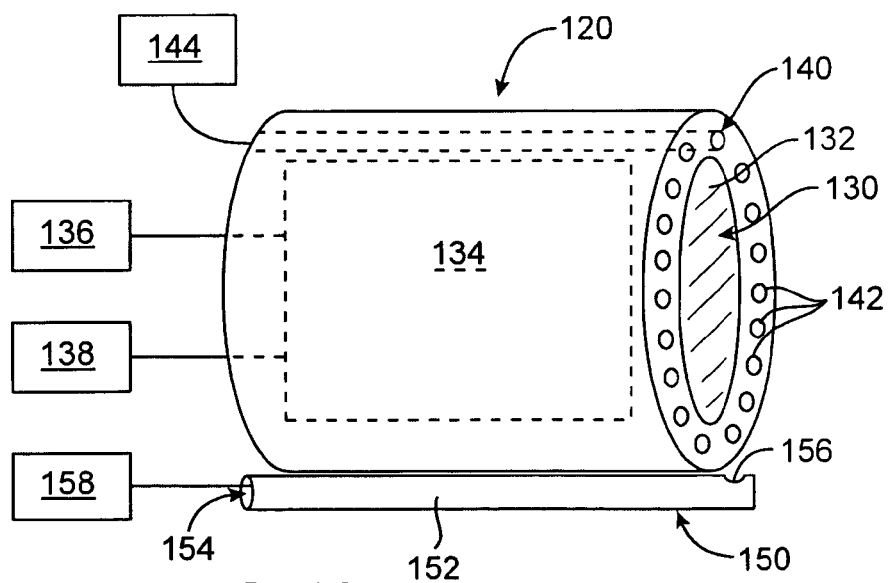
FIG. 10 is a detail view of an articulating element featuring visualization, illumination and flushing features.

With reference to FIG. 10, a combination articulating element is described that provides illumination, visualization and fluid flushing. Articulating element 120 comprises visualization element 130 having lens 132 and video chip 134 with an image sensor, such as a CCD or CMOS image sensor. The video chip is coupled to power source 136, as well as signal processing and/or display unit 138.

Element 120 further comprises illumination element 140 for illuminating a region of interest to facilitate visualization with element 130. Illumination element 140 comprises optical fibers 142, which are illustratively disposed in a ring about lens 132. Fibers 142 are coupled to light source 144.

Element 120 also comprises flushing element 150 for cleaning lens 132 of visualization element 130, as well as optical fibers 142 of illumination element 140. Flushing element 150 comprises tube 152 having lumen 154 that distally terminates at side port 156 disposed adjacent to lens 132. Tube 152 may be proximally coupled to fluid injection element 158, which may, for example, comprise a syringe filled with saline.

Figure 11:
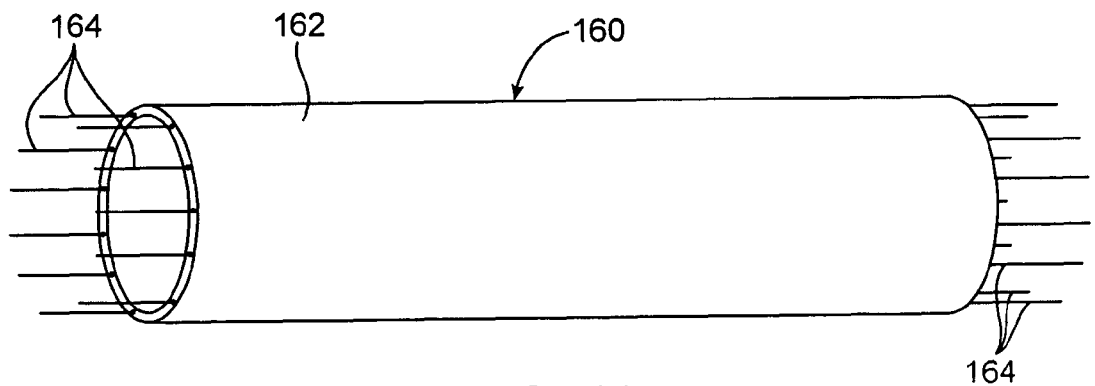
FIG. 11 is a schematic view of a liner for use with an elongate body, the liner adapted to carry control elements through the body.

Referring now to FIG. 11, a liner for use with an elongate body is described. Liner 160 comprises polymeric substrate 162 having control elements 164 embedded or disposed therein. Liner 160 may, for example, be disposed within the working lumen of an elongate body of the present invention, such as working lumen 16 of elongate body 12 of apparatus 10. Polymeric substrate 162 may seal the lumen and preclude contact between the elongate body and bodily fluids. Furthermore, control elements 164 may extend between proximally-disposed control, power, injection, processing, etc., units and a distally-disposed cable that communicates with an articulating element of the present invention. The control elements may comprise, for example, tension wires, electrical wires, optical fibers, fluid transport tubes, etc. The elements may be slidable relative to substrate 162, or may be fixed relative to the substrate. When the position of control elements 164 is fixed relative to the substrate, substrate 162 and elements 164 may be coextruded to form liner 160. It is expected that routing the control elements within a liner will save room, thereby allowing for a larger working lumen for a given delivery profile.

Figure 12:
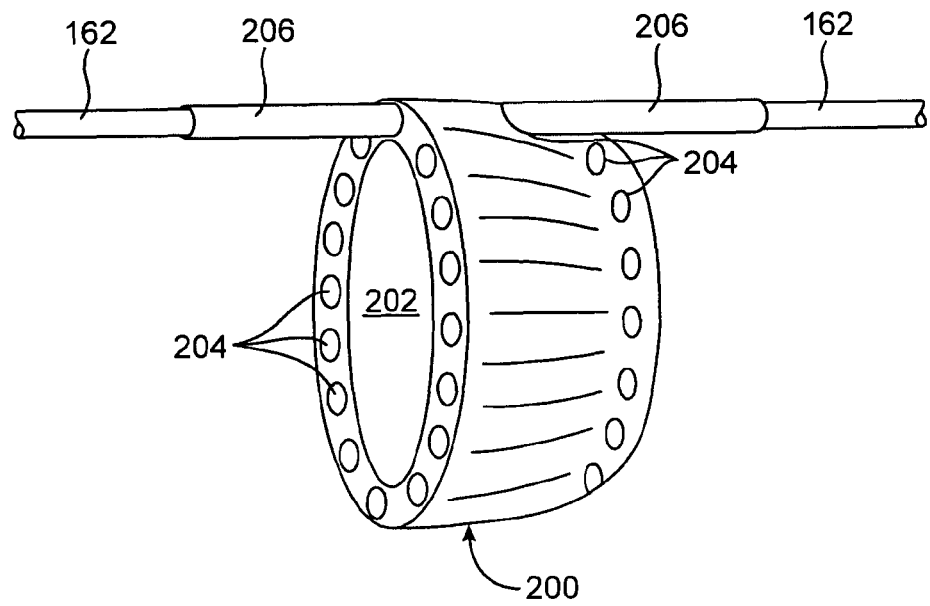
FIG. 12 is a schematic view of an exemplary link of an elongate body having through-holes for passage of control elements.

With reference to FIG. 12, alternative apparatus for routing control elements is described. FIG. 12 illustrates exemplary link 200 for an elongate body. A plurality of such links may be nested within one another to form the elongate body. Link 200 comprises working lumen 202 and through-holes 204. Control elements 162 may be routed through the through-holes. In FIG. 12, exemplary control element 162 is illustratively disposed within coil 206. Coil 206 may protect the control element during bending of an elongate body formed from a plurality of links 200. Furthermore, coil 206 may provide superior torqueability and/or pushability to such an elongate body.

One method for obtaining endoluminal access comprises advancing an elongate body or guide, as described above, into a body lumen or other cavity. The elongate body comprises an articulating element disposed near a distal region thereof, and the exemplary method further comprises articulating the articulating element from a position in-line with a working axis of the elongate body to a position out-of-line or off-axis from the working axis. Articulating the articulating element may expand the articulating element from a reduced delivery configuration to an expanded deployed configuration in a radially extended manner. Furthermore, articulating the element may expose the distal opening of a lumen through which a tool, fluid, suction, etc., may be advanced or withdrawn.

The method may further comprise imaging within the body lumen via an articulated visualization element. Such imaging may be stereoscopic, and the depth of field, field of view, focal point or depth, etc., of such imaging may be altered. Additionally, the method may comprise repositioning the articulating element in-line with the working axis of the elongate body and manipulating or removing the elongate body from the body lumen, as well as optionally re-articulating the element. The elongate body may be steered and/or rigidized while obtaining endoluminal access.

Although various illustrative embodiments are described above, it will be evident to one skilled in the art that various changes and modifications are within the scope of the invention. It is intended in the appended claims to cover all such changes and modifications that fall within the true spirit and scope of the invention.

What is claimed is:

1. Apparatus for endoluminal access comprising:
   an elongate body having a working axis and a distal region, the elongate body configured for insertion within a body lumen and comprising a plurality of links and at least one tensioning wire, with the elongate body having a first substantially flexible state and a second substantially rigid state;
   at least two working lumens extending through the elongate body;
   first and second articulating elements disposed near or at the distal region of the elongate body with the first articulating element pivotally connected to the elongate body near or at the distal region by a first linkage member pivotally connected to a first hinge on the first articulating element and a second hinge on the elongate body;
   a first visualization element on the first articulating element;
   a second visualization element on the second articulating element;
   wherein the first articulating element is movable from an in-line position to an off-axis position relative to the working axis of the elongate body, and wherein a distal opening of at least one of the working lumens is substantially covered by the first articulating element in the in-line position and is substantially uncovered by the first articulating element in the off-axis position.

2. The apparatus of claim 1 wherein the articulating elements are configured for independent off-axis articulation.

3. The apparatus of claim 1 wherein the articulating elements are configured for coordinated off-axis articulation.

4. The apparatus of claim 1 wherein a focal depth of the at least two visualization elements may be altered by altering a relative angle between the at least two visualization elements.

5. The apparatus of claim 1 further comprising a housing configured to couple the first articulating element to the elongate body and to facilitate articulation of the first articulating element.

6. The apparatus of claim 1 wherein the first articulating element is pivotally connected to the elongate body by a pair of pivoting parallel linkage members.

7. The apparatus of claim 1, wherein the elongate body is steerable.

8. The apparatus of claim 1 wherein at least one of the articulating elements further comprises a diagnostic or therapeutic tool.

9. The apparatus of claim 1 further comprising an atraumatic tip on the first articulatable element.

10. A method for obtaining endoluminal access, the method comprising:
    advancing an elongate body into a body lumen, with first and second articulatable elements disposed near or at a distal region of the elongate body;
    moving the first articulatable element from a position in-line with or adjacent to a working axis of the elongate body to a position out-of-line with the working axis, thereby at least substantially exposing a distal opening of a working lumen in the elongate body;
    stereoscopically viewing a surgical site within the body lumen; and
    passing a diagnostic or therapeutic tool through the working lumen while the first articulatable element is maintained in the out-of-line position.

11. The method of claim 10 with at least one of the visualization elements disposed within or upon the first articulatable element.

12. The method of claim 10 further comprising injecting or withdrawing a fluid through the working lumen.

13. The method of claim 10 further including articulating at least one of the articulatable elements by expanding it from a reduced delivery configuration to an expanded deployed configuration, and with the expanded articulatable element in a fixed position relative to the body.

14. The method of claim 10 further comprising repositioning the first articulating element in-line with or adjacent to the working axis of the elongate body, at a position in front of the elongate body.

15. The method of claim 14 further comprising manipulating the elongate body and moving the first articulatable element out-of-line with the working axis.

16. The method of claim 10 further comprising altering a focal depth during stereoscopic imaging.

17. The method of claim 10 further comprising steering the elongate body within the body lumen.

18. The method of claim 10 further comprising rigidizing the elongate body within the body lumen.

19. Apparatus for obtaining endoluminal access, comprising:
    a substantially flexible elongate body having a working axis and a distal region;
    at least two working lumens extending through the elongate body;
    first and second articulating elements, with the first articulating element disposed near or at the distal region of the elongate body and pivotally connected to the elongate body near or at the distal region by a linkage member pivotally connected to a first hinge on the first articulating element and a second hinge on the elongate body,
    wherein the first articulating element is movable from an in-line position to an off-axis position relative to the working axis of the elongate body, and wherein a distal opening of at least one of the working lumens is substantially covered by the first articulating element in the in-line position and is substantially uncovered by the first articulating element in the off-axis position; and the first and second articulating elements each having a visualization element, to provide stereoscopic visualization.

20. The apparatus of claim 19 wherein the articulating elements are configured for independent off-axis articulation.

21. The apparatus of claim 19 wherein the articulating elements are configured for coordinated off-axis articulation.

22. The apparatus of claim 19 wherein a focal depth of the at least two visualization elements may be altered by altering a relative angle between the at least two visualization elements.

23. The apparatus of claim 19 wherein the at least one articulating element is pivotally connected to the elongate body by a pair of pivoting parallel linkage members.

24. The apparatus of claim 19, wherein the elongate body is steerable.

25. The apparatus of claim 19, wherein the elongate body is rigidizable.

26. The apparatus of claim 19, wherein the at least one articulating element further comprises a diagnostic or therapeutic tool.

27. The apparatus of claim 19 further comprising an atraumatic tip on the first articulatable element.

* * * * *